United States Patent
Holzer et al.

(10) Patent No.: US 9,884,028 B2
(45) Date of Patent: *Feb. 6, 2018

(54) METHODS FOR TREATMENT OF BLADDER CANCER

(71) Applicant: Theracoat Ltd., D.N. Hefer (IL)

(72) Inventors: Asher Holzer, Haifa (IL); Dorit Daniel, RaAnana (IL); Eran Hirszowicz, Ramat-Gan (IL)

(73) Assignee: UroGen Pharma Ltd., Raanana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/683,901

(22) Filed: Apr. 10, 2015

(65) Prior Publication Data

US 2015/0209300 A1    Jul. 30, 2015

Related U.S. Application Data

(60) Continuation of application No. 13/726,162, filed on Dec. 23, 2012, now Pat. No. 9,011,411, which is a division of application No. 10/941,942, filed on Sep. 16, 2004, now Pat. No. 8,361,490.

(51) Int. Cl.

| | | |
|---|---|---|
| *A61K 9/00* | (2006.01) | |
| *A61K 9/70* | (2006.01) | |
| *A61M 25/10* | (2013.01) | |
| *A61M 31/00* | (2006.01) | |
| *A61K 35/74* | (2015.01) | |

(Continued)

(52) U.S. Cl.
CPC .............. *A61K 9/70* (2013.01); *A61K 9/0024* (2013.01); *A61K 9/0034* (2013.01); *A61K 31/7068* (2013.01); *A61K 35/74* (2013.01); *A61K 45/06* (2013.01); *A61L 31/145* (2013.01); *A61M 25/10* (2013.01); *A61M 31/00* (2013.01); *A61N 5/0603* (2013.01); *A61B 1/012* (2013.01); *A61B 5/4839* (2013.01); *A61M 25/04* (2013.01); *A61M 25/1011* (2013.01); *A61M 2025/0096* (2013.01);

(Continued)

(58) Field of Classification Search
CPC ...... A61K 9/70; A61K 31/7068; A61K 35/74; A61K 9/0034; A61K 45/06; A61K 9/0024; A61M 31/00; A61M 25/10; A61M 25/04; A61M 25/1011; A61M 2025/0096; A61M 2025/105; A61M 2210/1085; A61N 5/0603; A61L 31/145; A61B 1/012; A61B 5/4839
USPC ........ 424/426, 486; 604/21, 103.02, 517, 20
See application file for complete search history.

(56) References Cited

U.S. PATENT DOCUMENTS

| | | |
|---|---|---|
| 5,779,673 A | 7/1998 | Roth et al. |
| 5,849,035 A | 12/1998 | Pathak et al. |

(Continued)

OTHER PUBLICATIONS

Rodriguez-Valera F , (Biochemical Society Symposium, 1992, 58:135-147; abstract).*

(Continued)

*Primary Examiner* — Blessing M Fubara
(74) *Attorney, Agent, or Firm* — Greenberg Traurig, LLP

(57) ABSTRACT

Apparatus and methods for treatment of an internal cavity are provided. The internal cavity is coated with a treatment solution. The treatment solution can include a solidifiable matrix with or without a drug or combination of drugs incorporated therein, or a drug solution without a solidifiable matrix. The treatment solution is coated onto at least a portion of the internal cavity, and acts as a slow-release drug delivery system.

6 Claims, 8 Drawing Sheets

(51) Int. Cl.
- *A61B 1/012* (2006.01)
- *A61B 5/00* (2006.01)
- *A61N 5/06* (2006.01)
- *A61L 31/14* (2006.01)
- *A61K 31/7068* (2006.01)
- *A61K 45/06* (2006.01)
- *A61M 25/04* (2006.01)
- *A61M 25/00* (2006.01)

(52) U.S. Cl.
CPC ............... *A61M 2025/105* (2013.01); *A61M 2210/1085* (2013.01)

(56) References Cited

U.S. PATENT DOCUMENTS

| | | | |
|---|---|---|---|
| 5,914,345 A | 6/1999 | Slepian et al. | |
| 6,207,180 B1 * | 3/2001 | Ottoboni | A61K 9/0034 424/426 |
| 6,352,710 B2 | 3/2002 | Sawhney et al. | |
| 6,443,941 B1 | 9/2002 | Slepian et al. | |
| 6,689,200 B2 | 2/2004 | Scarborough et al. | |
| 8,361,490 B2 * | 1/2013 | Holzer | A61K 45/06 424/426 |
| 9,011,411 B2 * | 4/2015 | Holzer | A61K 45/06 424/426 |
| 9,040,074 B2 * | 5/2015 | Holzer | A61K 9/0024 424/426 |
| 2006/0127420 A1 * | 6/2006 | Chung | A61K 9/0019 424/400 |

OTHER PUBLICATIONS

Material Safety Data Sheet for Gemcitabine, 2011, Pfizer.*
J.Nakamura et al., "Water-soluble Taxol Conjugates with Dextran and Targets Tumor Cells by Folic Acid Immobilization", Anticancer Research 30: 903-910 (2010).
J.Lee et al., "Hydrotropic Solubilization of Paclitaxel: Analysis of Chemical Structures for Hydrotropic Property"; Pharmaceutical Research, vol. 20, No. 7, Jul. 2003.

* cited by examiner

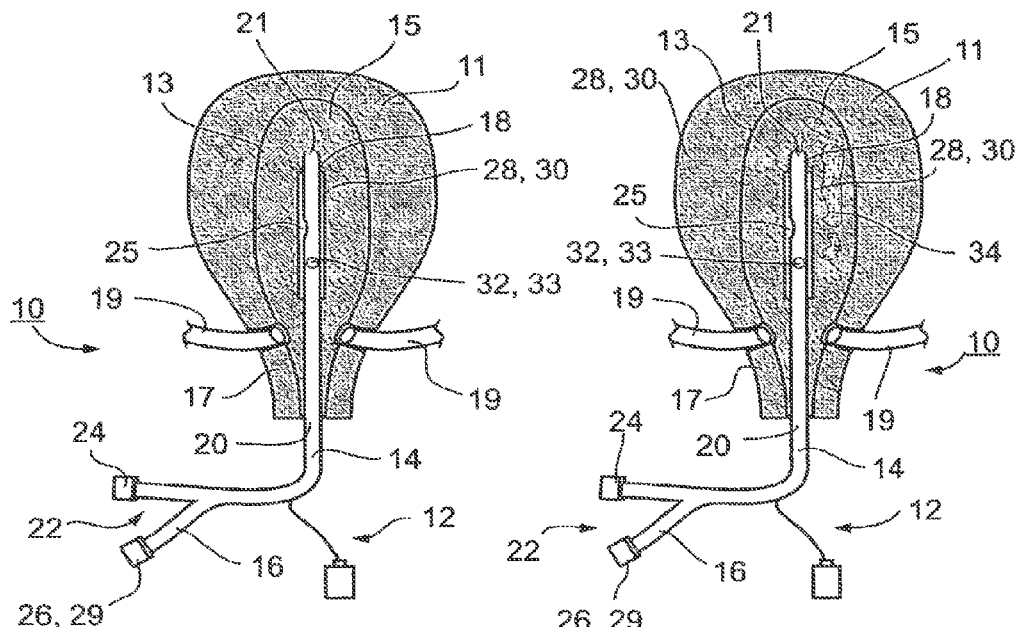
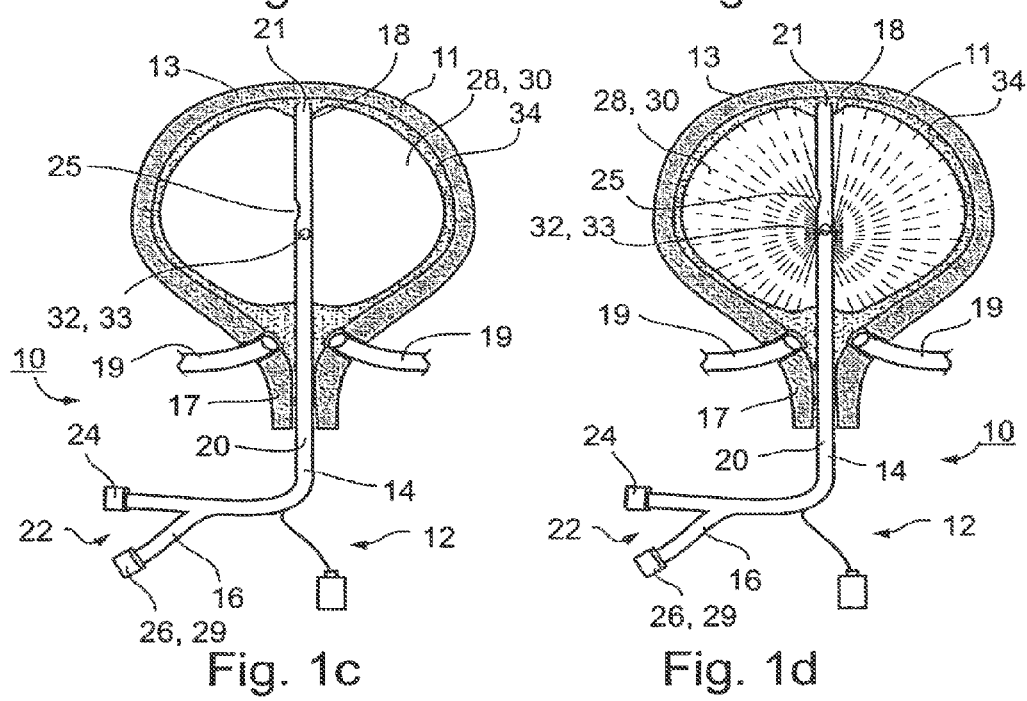

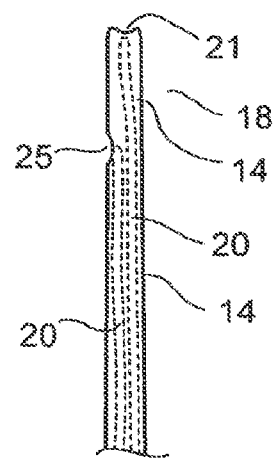
Fig. 2
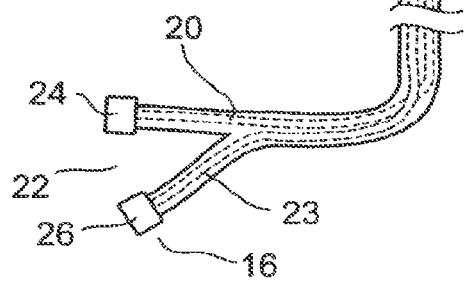
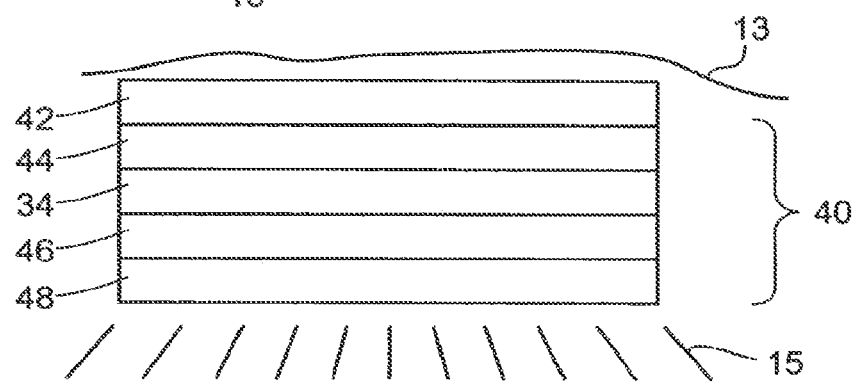
Fig. 3
Fig. 4a
Fig. 4b
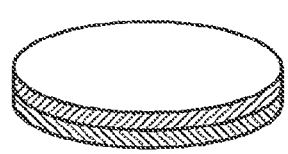
Fig. 4c

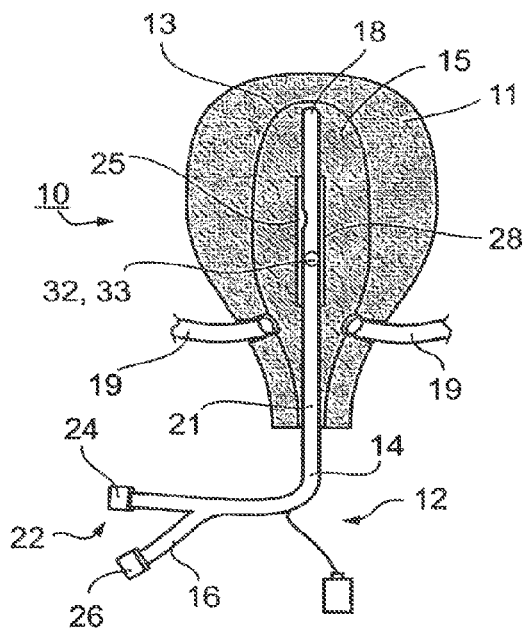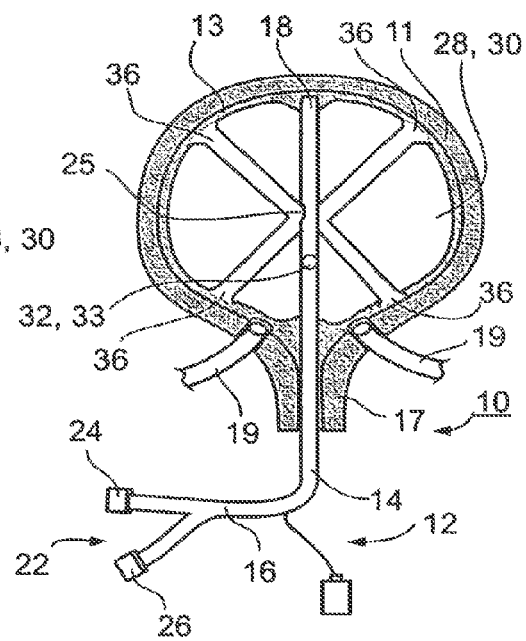
Fig. 5a　　　Fig. 5b
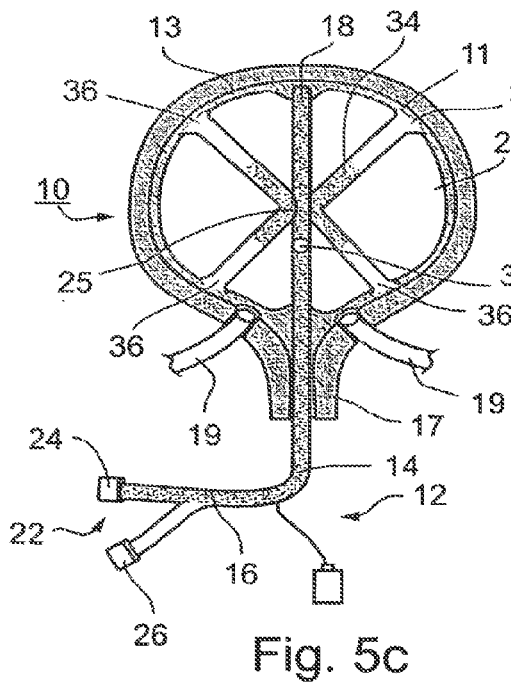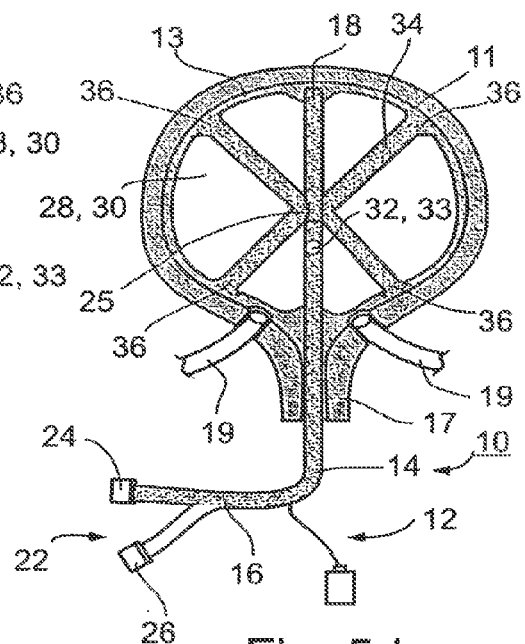
Fig. 5c　　　Fig. 5d

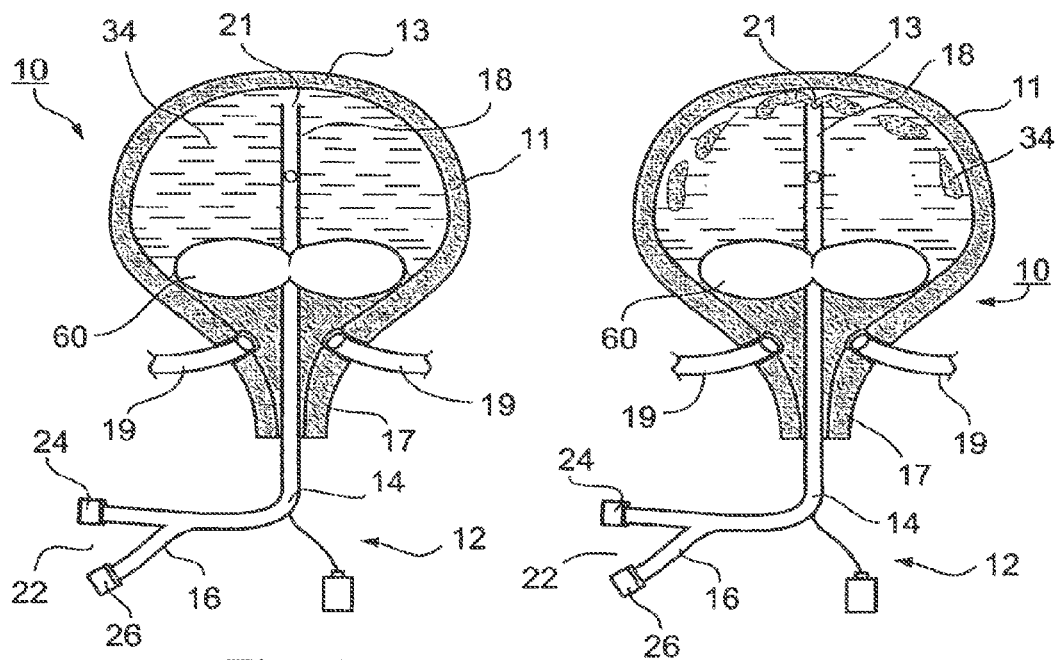
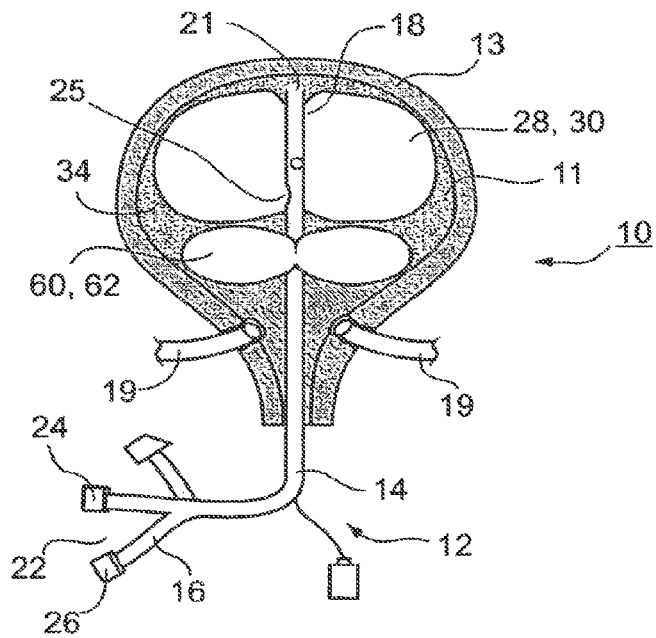

METHODS FOR TREATMENT OF BLADDER CANCER

RELATED APPLICATIONS

This application is a continuation of U.S. non-provisional patent application Ser. No. 13/726,162 filed on Dec. 23, 2014, now U.S. Pat. No. 9,011,411, which is a divisional of U.S. non-provisional patent application Ser. No. 10/941,942 filed Sep. 16, 2004 now U.S. Pat. No. 8,361,490, the entirety of which are hereby incorporated herein by reference.

FIELD AND BACKGROUND OF THE INVENTION

The present invention relates to biocompatible drag delivery methods and systems and, more particularly, to systems and methods for treating cancer of an internal cavity such as the urinary bladder.

The most common form of bladder cancer is transitional cell carcinoma (TCC), involving the cells that line the urinary tract, accounting for more than 90% of bladder cancers. One treatment for patients with early stage bladder cancer is surgical removal of the tumor, known as Trans-Urethral Resectomy (TUR). However, even after complete excision of a superficial bladder tumor, recurrence rates are up to 75%. Although most recurrences are also superficial, bladder cancer is a multi-focal disease and new tumors may not necessarily occur at the same location. Accordingly, a post-surgery monitoring program is always initiated for early detection of recurrence. The standard monitoring procedure typically includes flexible cystoscopic examinations of the bladder every three to four months for the first two years and, in the absence of recurrence, less frequently thereafter.

Flushing of the bladder with different drugs on a regular basis has been shown to significantly reduce the recurrence rate. Specifically, the commonly used agents include Bacillus Calmette-Guerin (BCG), thiotepa, doxorubicin, mitomycin C, Taxol™ and Gemzar™. However, multiple invasive sessions are needed on a regular basis.

Furthermore, it has been shown that during TUR, cells released during surgical excision of the tumor tend to migrate, which can lead to new sites of tumor formation. It would be advantageous to provide means for preventing such occurrences while treating the cancer as well.

The present invention seeks to remedy the deficiencies of the commonly used method of flushing the internal cavity, providing a more constant treatment while protecting unaffected areas.

SUMMARY OF THE INVENTION

According to one aspect of the present invention, there is provided a method for treatment of an internal cavity. The method includes incorporating a drug within a biocompatible matrix to form a treatment solution, providing the treatment solution to an interior wall of the cavity, and adjusting the treatment solution so as to provide optimal contact between the treatment solution and the interior wall.

According to another aspect of the present invention, there is provided a method for coating an internal cavity. The method includes providing an adapted endoscope, the adapted endoscope including a passageway for the fluid, wherein the passageway has a proximal end located outside of a body, and a distal end configured for insertion into the interior cavity, introducing the distal end into the interior cavity, and introducing the fluid through the passageway and into the internal cavity.

According to yet another aspect of the present invention, there is provided a method for treating bladder cancer. The method includes incorporating a cancer-fighting drug into a biocompatible matrix to form a drug carrier solution, introducing the drag carrier solution into the bladder, and coating at least a portion of the bladder with the drug carrier solution.

According to further embodiments, the method further includes curing at least a portion of the biocompatible matrix thereby providing a substantially rigid biocompatible drug carrier coating, and leaving the substantially rigid biocompatible drug carrier coating within the bladder for a specified period of time, during which time the cancer-fighting drug is releasable into the bladder.

According to yet another aspect of the present invention, there is provided a system for treatment of an internal cavity. The system includes a delivery device with a body having a proximal end and a distal end and a delivery channel formed through the body, an adjuster positioned on the distal end of the body, and a stabilizing mechanism positionable within the adjuster.

According to yet an additional aspect of the present invention, there is provided a method for preventing cell migration and adherence within an internal cavity during tumor resection. The method includes coating the internal cavity with a substance, and resecting the tumor through the coating. In one embodiment, the method further includes curing the substance prior to resecting said tumor.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1*a-d* are illustrations of a system positioned in a urinary bladder in accordance with a preferred embodiment of the present invention;

FIG. 2 is an illustration of a body of the system of FIGS. 1*a-d* shown in greater detail;

FIG. 3 is a schematic diagram of a configuration of a coating substance in accordance with a preferred embodiment of the present invention;

FIGS. 4*a-c* are schematic illustrations of possible configurations of a coating substance in accordance with several embodiments of the present invention;

FIGS. 5*a-d* are illustrations of a system in accordance with another embodiment of the present invention, further including a valve delivery channel;

FIG. 9 is an illustration of a system for flushing an internal cavity, in accordance with an embodiment of the present invention;

FIG. 10 is an illustration of a system for delivery of a matrix to an internal cavity, in accordance with an embodiment of the present invention; and FIG. 11 is an illustration of a combination system in accordance with another embodiment of the present invention.

DESCRIPTION OF THE PREFERRED EMBODIMENTS

Figure 6A:
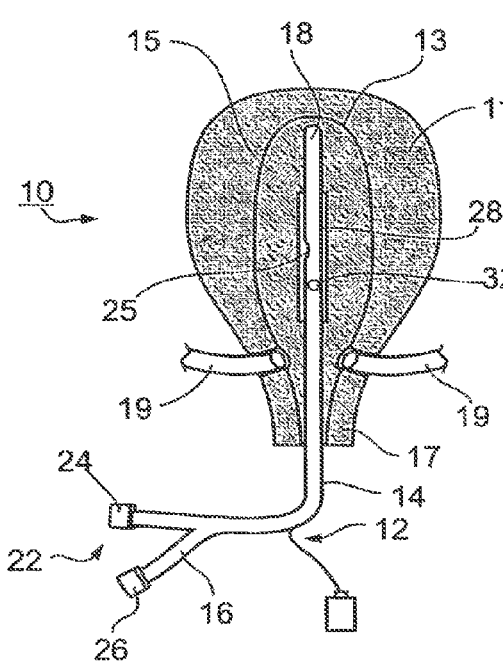
FIGS. 6*a-d* are illustrations of a system in accordance with yet another embodiment of the present invention, showing a rotating aspect.

The present invention is of systems and methods for treating an internal cavity by applying a treatment solution to a wall of the internal cavity. Specifically, the present invention can be used to treat the internal cavity by coating the wall with a treatment solution. The term "treatment solution" in the present application encompasses several different embodiments, including a solidifiable matrix with or without a drug or combination of drugs incorporated therein, or a drug solution without a solidifiable matrix, all of which are described in further detail hereinbelow. In a preferred embodiment, a drug or combination of drugs incorporated in a biodegradable polymer is coated onto at least a portion of the internal cavity, acting as a slow-release drug delivery system. The treatment solution can be distributed over an entire area or region for general treatment, or at a specific location for acute treatment.

The principles and operation of apparatus and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIGS. 1a-d, which are illustrations of a system 10 positioned in an organ in accordance with a preferred embodiment of the present invention. The organ illustrated herein is a urinary bladder 11; however, it should be readily apparent that all descriptions may apply to other organs as well, such as the intestines, stomach, a blood vessel, esophagus, appendix, duodenum, lungs, or any other internal cavity. Urinary bladder 11 has an internal wall 13, an internal cavity 15 and a neck 17. Ureters 19, which deposit urine into urinary bladder 11, are partially positioned within internal cavity 15. System 10 includes a delivery device 12 having a body 14 with a proximal end 16 and a distal end 18, and a delivery channel 20 formed through body 14. Delivery channel 20 includes an exit port 21 for communication with internal cavity 15, preferably located at or near a distal end of delivery channel 20. An adjustment channel 23 is also positioned through body 14, and includes an adjustment exit port 25 for communication with an adjustor 28. Proximal end 16 includes a hub 22 having a delivery port 24 and an adjustment port 26, and is positioned outside of bladder 11. A configuration of ports and channels in accordance with a preferred embodiment of the present invention is described in greater detail hereinbelow with respect to FIG. 2.

System 10 is Introduced through neck 17 of bladder 11, such that distal end 18 is substantially within bladder 11. Distal end 18 includes an adjustor 28, designed to adjust a treatment solution 34 introduced through delivery channel 20 within bladder 11, preferably adjusting the treatment solution so that, it is formed against and conforms to internal wall 13. In a preferred embodiment, adjuster 28 is an inflatable balloon 30 in fluid communication with inflation port 26 via adjustment channel 23 and adjustment exit port 25. In an alternative embodiment, adjustor 28 is a brushing mechanism, configured for brushing or spreading treatment solution 34 onto internal wall 13 such as, for example, an airbrush. Control of adjuster 28 is achieved from outside of urinary bladder 11 via adjustment port 26. In a preferred embodiment, adjustment port 26 is an inflation port 29, and balloon 30 is inflated or deflated by introduction and removal of a fluid into and out of inflation port 29. In a preferred embodiment, the fluid is a gas or a combination of gases, such as air. In an alternative embodiment, the fluid is saline. In yet another embodiment, the fluid is water or any other suitable liquid. Inflatable balloon 30 is depicted in FIGS. 1a and 1b in a deflated state, and in FIGS. 1c and 1d in an inflated state. In an alternative embodiment, adjustment port 26 includes a control mechanism for controlling adjustor 28, for example, a handle for manually controlling a brushing mechanism.

System 10 further includes a stabilizing mechanism 32 for stabilizing treatment solution 34 after it is introduced into urinary bladder 11 via delivery port 24 and adjusted within the bladder via adjustor 28. In a preferred embodiment, stabilizing mechanism 32 is a curing mechanism 33, wherein treatment solution 34 includes a curable biocompatible material, and wherein curing mechanism 33 allows at least a portion of treatment solution 34 to cure, forming a substantially rigid material within bladder 11. In a preferred embodiment, stabilizing mechanism 32 is a light source. In a preferred embodiment, stabilizing mechanism is positioned on body 14, such that upon insertion of body 14 into urinary bladder 11, stabilizing mechanism 32 is in place within bladder 11. In another embodiment, the light source is introduced via delivery channel 20, and body 14 is transparent. In an alternative embodiment, the light source is introduced through an additional channel, positioned either coaxial with or adjacent to delivery channel 20. A light source used for curing can be a source of electromagnetic radiation, for example, actinic light. In alternative embodiments, curing mechanism 33 is heat, pressure, or a curing agent or combination of curing agents. Any of the above curing mechanisms may be combined as well. Methods for curing polymers inside body lumens, suitable for the present invention, are disclosed in U.S. Pat. No. 5,849,035 to Pathak et al. and U.S. Pat. No. 5,779,673 to Roth et al., incorporated herein by reference in their entireties. In an alternative embodiment, no curing mechanism is present, and treatment solution 34 comprises self-coring material.

Reference is now made to FIG. 2, which is an illustration of body 14 of delivery device 12 in greater detail. Hub 22 located at proximal end 16 is positioned outside of the body, and includes two ports: delivery port 24 and adjustment port 26. Delivery port 24 is in fluid communication, via delivery channel 20, with exit port 21. As such, deliver/port 24 is configured for introduction of treatment solution 34 from outside of the body into internal cavity 15 of bladder 11. Adjustment port 26 is in communication, via adjustment channel 23, with adjustment exit port 25. As such, adjustment port is configured for controlling adjuster 28 via injection of a fluid such as air or saline, or via a mechanical method. In a preferred embodiment, adjuster 28 is a balloon 30, which can be inflated and deflated by introduction and removal of liquid or air through adjustment port 26. Delivery channel 20 and adjustment channel 23 are both formed within body 14 of delivery device 12, and may be positioned side by side, coaxially, or in any suitable manner so as to separately deliver the appropriate materials to each of exit ports 21 and 25.

A method of treating an internal cavity, in accordance with a preferred embodiment of the present invention, includes the following steps. Treatment solution 34 is introduced into bladder 11 and more specifically onto bladder wall 13 via delivery channel 20 and exit port 21, as shown in FIG. 1b. Introduction of treatment solution 34 into delivery channel is done by an infusion bag connected to delivery port 24 or by injection into delivery port 24. In a preferred embodiment, treatment solution 34 comprises a drag incorporated in a biocompatible matrix. In an exemplary preferred embodiment, the biocompatible matrix is a biodegradable polymer, which can be cured into a substantially rigid biodegradable substance coated on internal wall 13 of bladder 11. In alternative embodiments, treatment solution is a polymer without drugs or a drug solution without a polymer, as will be described in further detail hereinbelow. Treatment solution 24 is introduced by coating, spraying, smoothing or any other suitable method. After introduction of treatment solution 34 onto bladder wall 13, adjuster 28 is controlled via adjustment port 26. In a preferred embodiment, as shown in FIG. 1c, adjuster 28 is a balloon 30 and adjustment port 26 is an inflation port 29. Balloon 30 is inflated by introduction of a fluid through inflation port 29. In a preferred embodiment, the fluid is saline. In alternative embodiments, the fluid is air or water. Inflation of balloon 30 causes treatment solution 34 to be trapped between balloon 30 and internal wall 13. In this way, balloon 30 adjusts treatment solution 34 within bladder 11 by, for example, coating it onto internal wall 13, adjusting a thickness of the coating, and positioning it in appropriate locations. Balloon 30 may be inflated and deflated several times during the procedure in order to improve the spreading and homogeneity of the polymer on internal wall 13. Finally, treatment solution is stabilized via stabilizing mechanism 32 as shown in FIG. 1d. Stabilizing can include, for example, curing a curable polymer, solidifying a liquid through thermal, chemical, photochemical, or any other means, or in any way changing a physical form of treatment solution 34 such that its position and properties within bladder 11 are optimized. In an exemplary preferred embodiment, stabilizing mechanism 32 is a curing mechanism such as, for example, a light source. In alternative embodiments, curing is accomplished by adding a curing agent, or by applying a pressure to treatment solution 34. Treatment solution 34 may also be a self-curing material which is configured to self-cure shortly after it is introduced into bladder 11. In yet another embodiment, treatment solution 34 is comprised of at least two materials, the combination of which leads to curing thereof. Each of the at least two materials are either mixed together just before introduction into bladder 11 through delivery channel 20, or are each introduced separately, and mixed within bladder 11. Finally, balloon 30 is deflated and separated from treatment solution 34, and delivery device 12 is removed from bladder 11. If the coating is biodegradable, it will eventually degrade on its own, eliminating the need for further intervention. If the coating is biostable, it will generally require a separate intervention to remove the substance from the cavity, although it may be expelled naturally as well. In an alternative embodiment, balloon 30 is left inside bladder 11 for as long as necessary.

In another embodiment, a relatively heavy liquid is first introduced into bladder 11. A heavy liquid is defined as a liquid with a high molecular weight or a high gravitational weight. Treatment solution 34 is then introduced into bladder 11, wherein treatment solution 34 is lighter than the heavy liquid. When the patient stands up, the heavy liquid drops to the bottom of the bladder while treatment solution 34 remains at a top portion of bladder 11. The heavy liquid is, in a preferred embodiment, an oil-based liquid and treatment solution includes a water-based liquid, such that the two are configured to stay separate from one another. In this way, treatment solution 34 does not reach a bottom portion of bladder 11, including, for example, ureters 19.

In one embodiment, delivery device 12 is an adapted standard endoscope, which includes a delivery channel 20 as one of its lumens. A standard endoscope for use in the present application includes ones available, for example, from Bard Endoscopic Technologies, C.R, Bard Inc. (Billerica, Mass., USA) or Circon Corporation (Richmond, British Columbia, Canada), or any other source for a standard endoscope. By using an endoscope as a delivery vehicle, it is possible to delivery treatment solution 34 while performing a procedure, and while viewing the process through a viewing lens in the endoscope, This would be particularly useful when only specific areas of the bladder are targeted, such as after a tumor resection. Several lumens may be present within delivery device 12 including, for example, an irrigation channel, a viewing channel, a light source, a working channel and a delivery channel. In one embodiment, an endoscope is modified to provide a light guiding channel for delivering light of a variety of wavelengths, such as, for example, ultraviolet light.

In an alternative embodiment, treatment solution 34 Is applied to a balloon prior to introduction into bladder 11. Balloon 30 is then Inserted Into bladder 11 and inflated. Inflation of the balloon with treatment solution 34 thereon results in application of treatment solution 34 to internal wall 13.

In a preferred embodiment, several layers of materials are coated onto internal wall 13, in addition to treatment solution 34. For the purposes of description, the combination of layers is referred to herein as coating substance 40. Reference is now made to FIG. 3, which is a diagram of a configuration of coating substance 40 in accordance with a preferred embodiment of fee present invention. A first layer, termed adhesion layer 42, is closest to internal wall 13 and includes an agent to increase the adherence of treatment solution 34 to internal wall 13. Adhesion layer 42 has elasticity and an ability to expand and contract, thus conforming to the anatomical morphology of internal wall 13. An example of such an agent is an eosin based primer. A second layer is a buffering layer 44. Buffering layer 44 provides control over the amount and/or concentration of treatment solution 34 which reaches internal wall 13. This is done by manipulating the porosity, thickness and other relevant properties of buffering layer 44. An example of a material used for buffering layer 44 is cyanoacrylate. A third layer is comprised of treatment solution 34, coated onto adhesion and buffering layers 42 and 44. Details regarding possible compositions and configurations of treatment solution 34 are described in greater detail further hereinbelow. A fourth layer is a blocking layer 46, Blocking layer 46 is designed to control an amount and/or concentration of treatment solution 34 to reach an inner volume of the bladder. In one preferred embodiment, blocking layer 46 is configured to completely prevent treatment solution 34 from reaching internal cavity 15. In alternative embodiments, blocking layer 46 is configured to allow some amount of treatment solution 34 to reach internal cavity 15. In one preferred embodiment, blocking layer 46 is a high molecular weight PEG-lactide diacrylate hydrogel. A fifth layer is a separation layer 48, which can reduce adhesion of the matrix to delivery device 12 and/or adjuster 28. This layer is virtually non-adhesive, a property which may be achieved by polymer casting or curing. Separation layer 48 prevents adhesion when, for example, balloon 30 is removed from bladder 11 and when bladder 11 is collapsed. An example of a material used for separation layer 48 is cyanoacrylate. Any or all of the layers described above with reference to FIG. 3 may be used alone or in combination in accordance with the present invention. Furthermore, some or all of the layers may be combined into a polymer matrix and applied to internal wall as a unit. Alternatively, each layer is introduced separately into bladder 11 via delivery channel 20, or via additional channels which can be included within system 10. In a preferred embodiment, at least one of the layers is biodegradable.

Many different configurations of coating substance 40 are possible. Reference is now made to FIGS. 4a-c, which are schematic illustrations of possible configurations of coating substance 40 in accordance with several embodiments of the present invention. In one embodiment as shown in FIG. 4a, coating substance 40 is a polymer patch, having a middle portion 41 and an edge portion 43. Middle portion 41 includes treatment solution 34, while edge portion 43 includes adhesion layer 42 or any type of adhesive substance which enables coating substance 40 to attach to internal wall 13. Other layers may be included as well. According to another embodiment, as shown in FIG. 4b, an entire surface 45 includes an adhesive portion and treatment solution combined. According to yet another embodiment as shown in FIG. 4c, a multi-layer coating substance includes several layers, each with varying drug concentrations.

Reference is now made to FIGS. 5a-d, which are illustrations of system 10 in accordance with another embodiment of the present invention wherein system 10 includes a valve delivery channel 36 instead of or in addition to delivery channel 20. Valve delivery channel 36 allows treatment solution 34 to be introduced into internal cavity 15 in various locations, and not solely through one delivery channel 20 as in the previously described embodiment, thus providing improved spreading of treatment solution 34. In one embodiment, delivery channel 20 separates into several channels, each of which is formed through balloon 30 to form valve delivery channel 36. Each section of valve delivery channel 36 provides a different section of bladder 11 with treatment solution 34. In another embodiment, several channels are directly connected to one or more ports at proximal end 16.

A method of delivering treatment solution 34 to internal cavity 15 using valve delivery channel is described with reference to FIGS. 5a-d. As shown in FIG. 5a, system 10 is introduced into bladder 11, with balloon 30 in an unexpanded state. Next, as shown in FIG. 5b, balloon 30 with valve delivery channel 36 therethrough is expanded via inflation port 26. Once balloon 30 is expanded, treatment solution 34 is introduced through valve delivery channel 36 and onto bladder wall 13, shown in FIGS. 5c and 5d. Balloon 30 may be inflated and deflated as many times as necessary for smoothing and improved spreading of treatment solution 34. Treatment solution 34 will naturally fill in the gaps and be positioned in between balloon 30 and internal wall 13. Treatment solution is stabilized via stabilizing mechanism 32 as shown and described in detail with reference to FIG. 1d above. Finally, balloon 30 is deflated and separated from treatment solution 34, and delivery device 12 is removed from bladder 11. In an alternative embodiment, balloon 30 is left inside bladder 11 for as long as necessary.

Figure 6B:
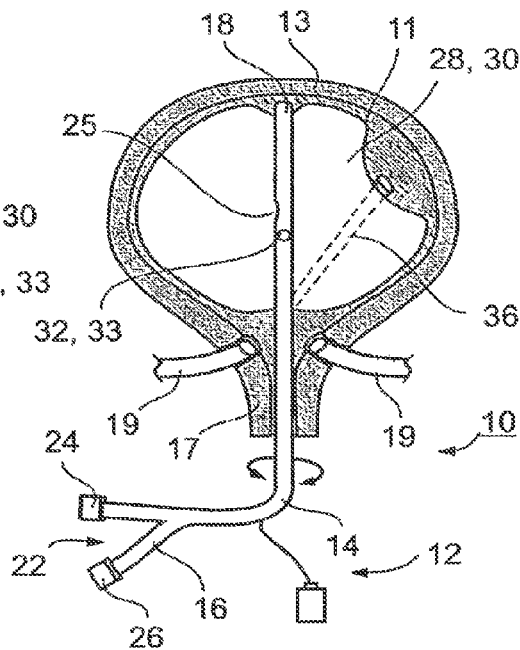

Reference is now made to FIGS. 6a-d, which are illustrations of system 10 in accordance with yet another embodiment of the present invention. As shown in FIG. 6b, a single valve delivery channel 36 is positionable within system 10, and is rotatable around an axis. In a preferred embodiment, a section of balloon 30 is removed, the thickness of which defines a thickness of a delivered amount of treatment solution 34, The embodiment disclosed in FIGS. 6a-d allows for bursts of delivery of treatment solution 34 into specific areas of bladder 11. Furthermore, delivery channel 36 is rotatable about an axis, providing a controllable amount of treatment solution application at any point around an inner circumference of internal wall 13.

Figure 6C:
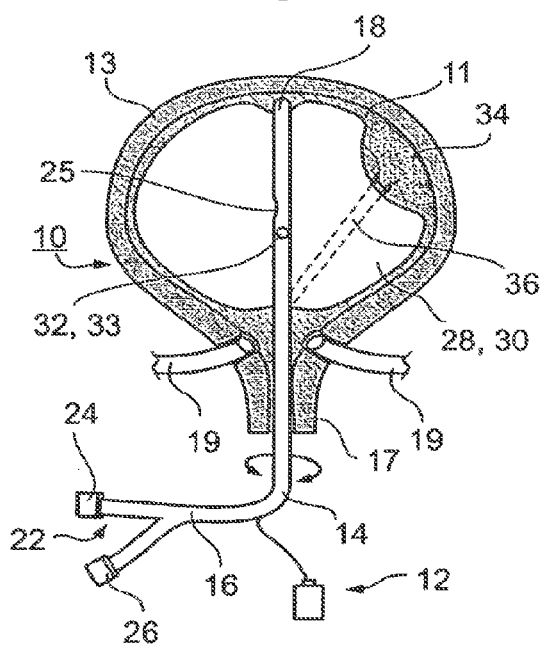
Figure 6D:
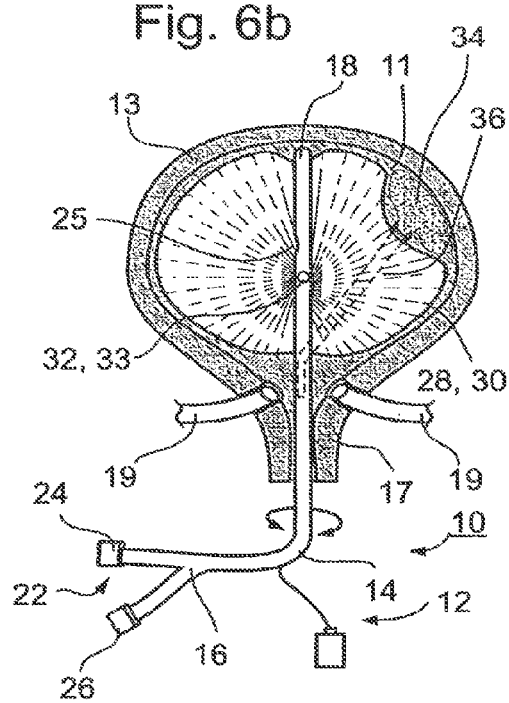

A method of delivering treatment solution 34 to internal cavity 15 using single valve delivery channel 36 is described with reference to FIGS. 6a-d. System 10 is placed through neck 17 of bladder 11 and positioned within internal cavity 15. Balloon 30 is then expanded, as shown in FIG. 6b. Treatment solution 34 is introduced into bladder 11 via delivery channel 36, positioned through balloon 30 such that treatment solution 34 exits through delivery channel and into an inner space between balloon 30 and internal wall 13, as shown in FIG. 6c. In one embodiment, balloon 30 has a smaller diameter in the area of delivery channel 36 to allow for an increased amount of treatment solution 34 to collect in that space. In another embodiment, balloon 30 has a variable geometry so as to predefine an area of application. System 10 can men be rotated up to 360 degrees, with introduction of additional treatment solution 34 occurring at predetermined times. In one embodiment, treatment, solution 34 is introduced during the entire time of the rotation of system 10, providing extensive coverage within the parameters of the balloon dimensions and geometry. In another embodiment, treatment solution is introduced only at specific times, resulting in coverage at specific locations. It should be noted that rotation capabilities may be included in any of the other described embodiments as well. Stabilizing mechanism 32, depicted herein as a curing light, is activated as shown in FIG. 6d. Finally, balloon 30 is deflated and separated from treatment solution 34, and delivery device 12 is removed from bladder 11.

Figure 7:
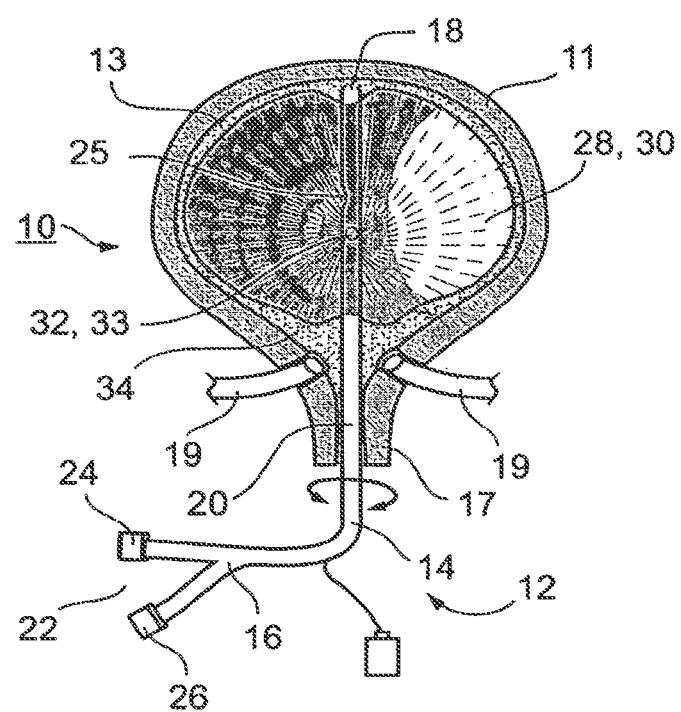
FIG. 7 is an illustration of a system in accordance with an alternative embodiment, wherein a stabilizing mechanism is activatable over a specific area within a bladder.

Reference is now made to FIG. 7, which is an illustration of system 10 in accordance with an alternative embodiment. Stabilizing mechanism 32 Is activatable over only a specific area within bladder 11. Thus, although treatment solution 34 may be applied throughout, an entire internal area of bladder 11, only one portion of treatment solution 34 is stabilized. Providing partial stabilization and/or curing may be accomplished by, for example, illuminating only a certain portion of bladder 11 with optical collimator lenses. Alternatively, adjustments to balloon 30 may provide partial stabilization by, for example, partially coating balloon 30 with an opaque substance while the remainder of balloon 30 is transparent to a curing light. System 10 can also be rotated up to 360 degrees, with stabilization occurring at predetermined times. In one embodiment, stabilization is done during the entire time of the rotation of system 10, providing extensive curing. In another embodiment, stabilization is done only at specific times. In a preferred embodiment, treatment solution 34 is a mixture of a drug or drugs incorporated within a biocompatible polymer matrix, wherein the matrix is curable by, for example, a light source. By controlling the emittance area of the light source, the amount of cured matrix can be controlled. This can be done at predetermined locations within bladder 11.

A method of stabilizing treatment solution 34 or coating substance 40 is described with reference to FIG. 7. Treatment solution 34 is introduced via delivery channel 20 and exit port 21 to internal cavity 15. Alternatively, treatment solution 34 or coating substance 40 is introduced via other delivery channels described in accordance with other embodiments of the present invention, such as valve delivery channel 36, for example. Once treatment solution 34 is within bladder 11, balloon 30 is inflated so as to smooth or spread treatment solution onto internal wall 13. A specified area is then stabilized. In a preferred embodiment stabilization is curing and is accomplished by exposure of one specific area of treatment solution 34 to a curing mechanism, such as a light source, a heat source or a curing agent. System 10 can also be rotated so as to provide, curing and/or stabilization at several specific areas of treatment solution 34. Finally, balloon 30 is deflated and separated from treatment solution 34, and delivery device 12 is removed from bladder 11.

Figure 8A:
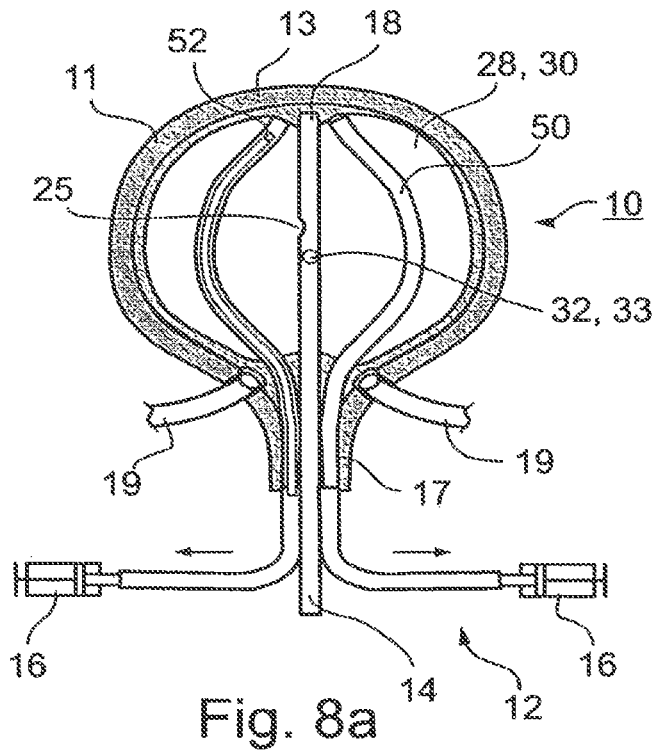
FIGS. 8a-c are illustrations of a system in accordance with yet another embodiment of the present invention, wherein tubes are situated on top of a balloon.
Figure 8B:
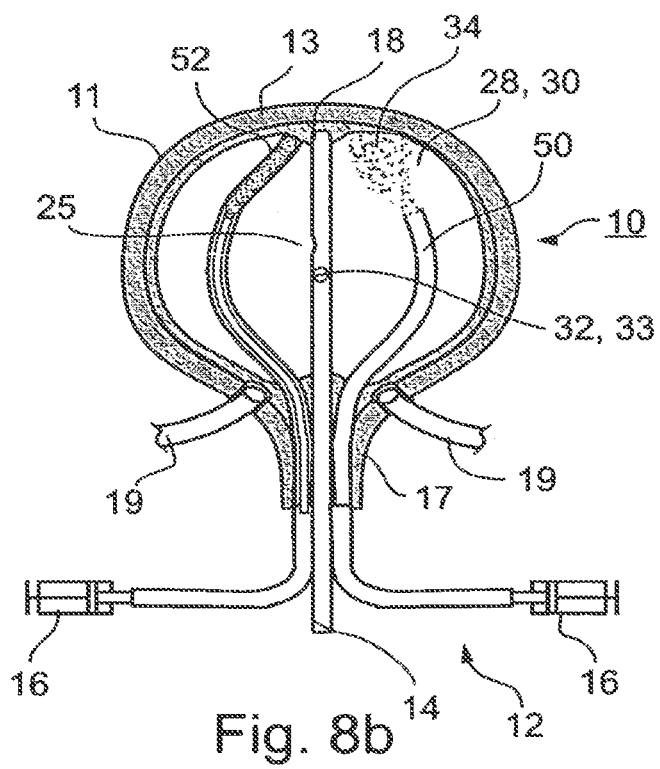
Figure 8C:
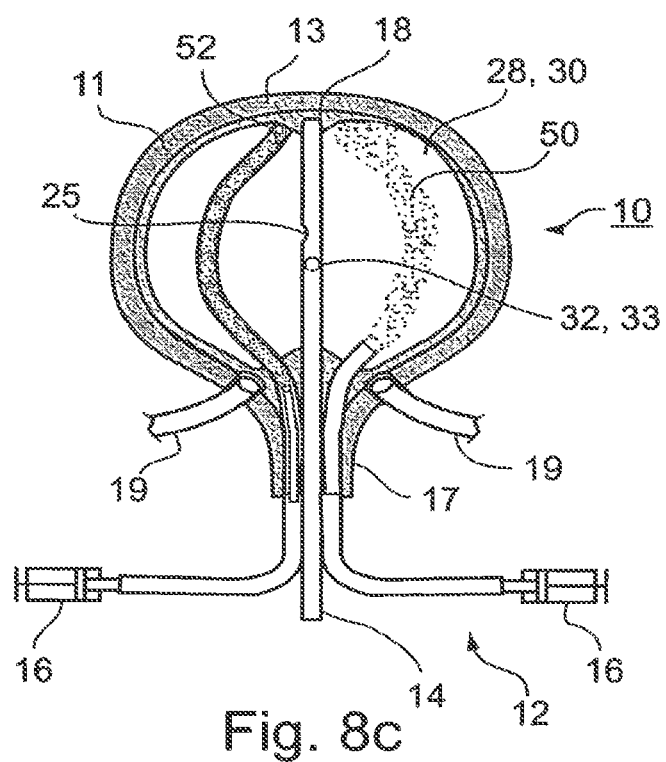

Reference is now made to FIGS. 8a-c, which are illustrations of system 10 in accordance with yet another embodiment of the present invention. Delivery device 12 includes at least one external channel 50, positioned on an exterior portion of balloon 30 and movable with respect to balloon 30. In a preferred embodiment, pressure can be applied to channel 50, thereby causing material contained within channel 50 to be pushed out. The pressure is controllable from outside the body, either by manual means or via a strain release mechanism (not shown). The strain release mechanism may be, for example, a cap or a ring positioned on a proximal end of channel 50. When balloon 30 is in an inflated state, external channel 50 is squeezed between balloon 30 and internal wall 13. A distal end of external channel 50 is initially located at a top portion of balloon 30. As treatment solution 34 is introduced, external channel 50 is pulled proximally, and strain release mechanism causes treatment solution to be squeezed out of channel 50 and onto balloon 30. In another embodiment, external channel 50 is positioned within a groove 52 formed in a body of balloon 30. Thus, an exact path of treatment solution delivery can be mapped out, providing many different options for coverage. For example, if groove 52 is formed in a zigzag configuration, treatment solution 34 will be delivered and spread in approximately the zigzag configuration, providing more coverage than a straight, line. Any other shape for groove 50 can be envisioned and is included within the scope of the present invention. Furthermore, external channel 50 can include any number of external channels.

A method of delivering treatment solution 34 to internal cavity 15 using external channels 50 is described with reference to FIGS. 8a-c. First, treatment solution 34 is introduced into external channels 50. One or several external ports provide access to external channels 50 from outside the body. Once treatment solution 34 is fully located within external channels 50, balloon 30 is inflated. External channels 50 are then pulled in a proximal direction, either one by one or simultaneously. By providing pressure either manually or via strain release mechanism, treatment solution 34 is released as external channels 50 are pulled back. During the procedure, balloon 30 may be inflated and deflated as many times as necessary, until treatment solution is sufficiently distributed onto internal wall 13. Stabilization is then done, as described above, followed by deflation of balloon 30 and removal of delivery device 12 from bladder 11. Three stages of pulling are shown in FIGS. 8a-c.

Reference is now made to FIG. 9, which is an illustration of a system 10 for delivery of treatment solution 34 in accordance with another embodiment of the present invention. Treatment solution 34 is a drug solution, and does not include a polymer or curable matrix. In this embodiment, treatment solution 34 is designed as a wash for bladder 11. In a preferred embodiment no adjustor 28 is included, since treatment solution 34 is designed to flow freely within internal cavity 15. Delivery device 12 further includes a stopper 60, designed to prevent treatment solution 34 from blocking ureters 19. Stopper 60 is positioned on body 14 of delivery device 12. In a preferred embodiment, stopper 60 includes inflatable balloons, which are deflated daring introduction of delivery device 12 into bladder 11 and inflated prior to introduction of treatment solution 34. In alternative embodiments, stopper 60 is a double-J stopper or of a pig-tail configuration, a ureter catheter, or any other mechanism for blocking.

A method of treating a bladder 11 in accordance with an embodiment of the present invention is described with reference to FIG. 9. First, delivery device 12 is inserted into bladder 11. Next, stopper 60 is activated. In one embodiment, activation of stopper 60 is via inflation of balloons. In another embodiment, activation of stopper 60 is via a mechanical mechanism, such as removal of a sheath for release of stopper 60. Treatment solution 34 is then introduced into bladder 11 and allowed to flush internal cavity 15. Finally, stopper 60 is deactivated, either by deflation of balloons or by mechanical means, and delivery device 12 is removed from the bladder. Treatment solution 34 then flows out of the bladder automatically.

Reference is now made to FIG. 10, which is an illustration of a system 10 for delivery of treatment solution to a bladder 11 in accordance with another embodiment of the present invention. Treatment solution 34 is a polymer solution, with or without a drug or drug combination incorporated within. Treatment solution is introduced via delivery channel 20 and allowed to spread freely within internal cavity 15. Delivery device 12 further includes a stopper 60, designed to prevent treatment solution 34 from blocking ureters 19. Stopper 60 is positioned on body 14 of delivery device 12. In a preferred embodiment, stopper 60 includes inflatable balloons, which are deflated during introduction of delivery device 12 into bladder 11 and inflated prior to introduction of treatment solution 34. In alternative embodiments, stopper 60 is a double J stopper or of a pig-tail configuration is a double-J stopper or of a pig-tail configuration, a ureter catheter, or any other mechanism for blocking.

A method of treating an internal cavity 15 in accordance with an embodiment of the present Invention is described with reference to FIG. 10. First, delivery device 12 is inserted into internal cavity 15. Next, stopper 60 is activated. In one embodiment, activation of stopper 60 is via inflation of balloons. In another embodiment, activation of stopper 60 is via a mechanical mechanism, such as removal of a sheath for release of stopper 60. Treatment solution 34 is then introduced into bladder 11 and allowed to spread freely. Next, stabilizing mechanism 32 stabilizes treatment solution 34. In a preferred embodiment, stabilization is curing and is done by a curing mechanism such as a light source, a heat source, or a curing agent. Alternatively, treatment solution 34 is self-curing. Stopper 60 is then deactivated, either by deflation of balloons or by mechanical means, and delivery device 12 is removed from the bladder. In one embodiment, treatment solution 34 does not include a drug or drug combination, and is used for coating internal surface 13. In another embodiment, treatment solution 34 does include a drug or drug combination as described in further detail hereinbelow.

Reference is now made to FIG. 11, which is an illustration of a system 10 in accordance with yet another embodiment of the present invention. System 10 includes a delivery device 12 having a proximal end 16, a distal end 18 and a body 14 connecting proximal and distal ends 16 and 18. Adjuster 28 is positioned at distal end 18. In a preferred embodiment, adjustor 28 is a balloon 30, in fluid communication with adjustment port 26, as described above with reference to FIG. 2. Further, stopper 60 is positioned on body 14, proximal to adjustor 28. In a preferred embodiment, stopper 60 is a stopper balloon 62, having an inflation channel which is separate from adjustment channel 23 and is controlled separately via a stopper port 64. In alternative embodiments, stopper 60 is a double-J stopper or of a pig-tail configuration, a ureter catheter, or any other mechanism for blocking.

A method of treating an internal cavity 15 in accordance with an embodiment of the present invention is described with reference to FIG. 11. First, delivery device 12 is inserted into internal cavity 15. Next, stopper 60 is activated. In one embodiment, activation of stopper 60 is via inflation of balloons. In another embodiment, activation of stopper 60 is via a mechanical mechanism, such as removal of a sheath for release of stopper 60. Treatment solution 34 is then introduced into bladder 11 and allowed to spread freely. Adjustor 28 is then activated so as to adjust treatment solution 34 within internal cavity 15. In a preferred embodiment, adjustor 28 is a balloon, which can be inflated and deflated as needed so as to provide optimum spreading of treatment solution 34. Next, stabilizing mechanism 32 stabilizes treatment solution 34. In a preferred embodiment, stabilization is curing and is done by a curing mechanism such as a light source, a heat source, or a curing agent. Alternatively, treatment solution 34 is self-curing. Balloon 30 is then deflated. Stopper 60 is then deactivated, either by deflation of balloons or by mechanical means, and delivery device 12 is removed from the bladder. It should be readily apparent that any of the embodiments described herein may be combined with a stopper such as the one described in reference to FIG. 12.

Alternative methods for preventing blockage of ureters 19 are also possible. For example, ureter catheters can be inserted prior to insertion of delivery device 12. Alternatively, stoppers can be inserted prior to insertion of delivery device 12. In an alternative method, a patient can be relieved of urine prior to stabilization of treatment solution 34. In an alternative embodiment, a heavy liquid solution introduced into bladder 11 prevents treatment solution 34 from reaching and blocking ureters 19. Alternatively, when selective application of treatment solution and/or stabilization thereof is performed, such as described above with reference to FIGS. 6a-c, 7 and 8a-b, it is possible to deliberately avoid application and/or stabilization of treatment solution 34 at the locations of the ureter orifices, thereby protecting the orifices. If internal cavity 15 is a cavity other than bladder 11, any other branching member can be similarly protected.

In one embodiment of the present invention, treatment solution 34 is used to coat an internal cavity prior to surgical removal of a cancerous tumor, so as to prevent cell migration from causing a new cancerous growth elsewhere in the cavity. Treatment solution 34 includes a curable matrix with or without drugs. Treatment solution 34 is applied to an entire internal wall 13 and optionally cured as described with respect to the embodiments above. When a transparent matrix is used, such as a hydrogel, for example, removal of the tumor can be done through the coating. Thus, the covered areas are protected from cell migration. The resected area can then be recoated, if desired, according to any of the methods described above.

In an alternative embodiment of the present invention, treatment solution 34 is used to treat an ulcer of the stomach. Treatment solution 34 is applied to the specific location of the ulcer within the stomach, in accordance with one of the embodiments described above, wherein selective application of treatment solution 34 is possible. In a preferred embodiment, for treatment of stomach ulcers, treatment solution 34 is comprised of a halobacter bacteria with an antibiotic in a polymer gel.

Treatment Solution:

Treatment solution 34 comprises a solidifiable matrix with or without a drug or combination of drugs incorporated therein, or a drug solution without a solidifiable matrix. In a preferred embodiment, treatment solution 34 comprises a drug or drug combination incorporated into a biocompatible matrix. The drug may be dissolved or dispersed therein. In one embodiment, the drug or drag combination is incorporated within the matrix prior to delivery through system 10. In an alternative embodiment, the drug or drug combination is mixed with the matrix once it is within bladder 11 by separate introduction into internal cavity 15. In a preferred embodiment, the biocompatible matrix is a polymer matrix, which can be chemically or physically altered while in vivo. Such alterations include, but are not limited to solidification, curing, cross-Sinking and the like. Examples of such polymers are well known in the art, and may include, for example, carboxylic acids such as glycolic acid and lactic acid, polyurethanes, polyesters such as poly(ethlene terephthalate), polyamides such as nylon, polyacrylonitriles, polyphosphazines, polylactones such as polycaprolactone, and polyanhydrides such as poly[bis(p-carboxyphenoxy) propane anhydride] and other polymers or copolymers such as polyethylene, polyvinyl, chloride and ethylene vinyl acetate. The polymers can include hydrophobic and hydrophilic polymers.

Other bioabsorbable polymers could also be used either singly or in combination, such as homopolymers and copolymers of delta-valerolactone, and p-dioxanone as well as their copolymers with caprolactone. Further, such polymers can be cross-linked with bis-caprolactone. Any of the commonly known drug carrier polymeric materials may be used as well, such as polyanhydrides. Examples of biodegradable polymer matrix materials which are suitable for use in the present application are disclosed in U.S. Pat. No. 5,914,345 to Slepian et al., U.S. Pat. No. 6,443,941. to Slepian et at, U.S. Pat. No. 6,689,200 to Scarborough et al. and U.S. Pat. No. 6,352,710 to Sawhney et al., incorporated by reference herein in then entireties.

In an alternative embodiment, biostable polymers can be used. Examples of biostable polymers are PVP, polyurethane, or any other biocompatible polymer. Since biostable polymers will not degrade in the body, they will need to be retrieved separately after the treatment process is complete. Alternatively, such a material may be naturally released from the body a little at a time.

In a preferred embodiment, the drug is an anti-cancer agent, which can include but is not limited to Bacillus Calmette-Guerin, thiotepa, doxorubicin, Gemzar™, Mitomicin C, epirubicin, thiotepa, or Taxol™. Other therapeutic agents may be included as well, including, for example, an antibiotic for treatment of intra-cavity ulcer, gastritis, colitis etc. Gemzar™ is a commercially available form of gemcitabine (2', 2'-difluoro-deoxycytidine, dFdC), which is a pyrimidine analogue of deoxycytidine in which the deoxyribose moiety contains two fluorine atoms at the 2'-position. (See Heinemann et al. Cancer Res 1988 48:4024). Taxol™ is a commercially available form of paclitaxel.

In a preferred embodiment, treatment solution 34 comprises Gemzar™ with polyethylene glycol, biodegradable polylactic acid, thimethylene carbonated and polymerizable acrylic ester. In an alternative embodiment, treatment solution 34 includes an antibiotic in a polymer matrix. In an alternative embodiment, treatment solution 34 includes a halobacter bacterium in a polymer gel matrix. It should be apparent that any combination of drugs and carriers can be used and are included in the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating urinary bladder cancer comprising:
    a) obtaining a treatment solution consisting of:
        (i) at least one anticancer agent,
        (ii) at least one polymer,
        (iii) water, and
        (iv) optionally at least one of:
            (a) an antibiotic or
            (b) a halobacter bacterium;
    b) administering the treatment solution directly to an internal wall of a urinary bladder of a human in need thereof;
    c) coating at least a portion of the internal wall of the urinary bladder of the human with the treatment solution; and
    d) stabilizing the treatment solution in the urinary bladder of the human without contact with urine.

2. The method of claim 1, wherein the anticancer agent is selected from the group consisting of bacillus calmett-guerin, thiotepa, doxorubicin, halobacter, gemcitabine, mitomycin C, epirubicin, paclitaxel and any combination thereof.

3. The method of claim 2, wherein the anticancer agent is gemcitabine.

4. The method of claim 1, wherein the at least one polymer is at least one of:
    at least one hydrophilic polymer or
    at least one hydrophobic polymer.

5. The method of claim 1, wherein the at least one polymer is at least one of glycolic acid, polylactic acid, polyurethanes, polyphosphazines, polycaprolactone, poly[bis(pcarboxyphenoxy) propaneanhydride], polyethylene glycol, trirnethylene carbonated and polymerizable acrylic ester, homopolymers and copolymers of delta-valerolactone, and p-dioxanone, copolymers of delta-valerolactone, and p-dioxanone and caprolactone, deltavalerolactone, and p-dioxanone cross-linked with bis-caprolactone, polyanhydrides, or polyvinylpyrrolidone.

6. The method of claim 5, wherein the anticancer agent is gemcitabine and the at least one polymer is polyethylene glycol, polylactic acid, and trimethylene carbonated and polymerizable acrylic ester.

* * * * *